United States Patent [19]

Ceriani et al.

[11] Patent Number: 4,572,901

[45] Date of Patent: Feb. 25, 1986

[54] METHOD AND COMPOSITION FOR PROTEIN IMMOBILIZATION

[75] Inventors: Roberto L. Ceriani, Lafayette; Jerry A. Peterson, Oakland, both of Calif.

[73] Assignee: Children's Hospital Medical Center of Northern California, Oakland, Calif.

[21] Appl. No.: 507,430

[22] Filed: Jun. 23, 1983

[51] Int. Cl.$^4$ ............... G01N 33/544; G01N 33/545; G01N 1/48; A61K 9/38
[52] U.S. Cl. .................................. 436/528; 422/57; 424/36; 436/531; 436/810; 436/823
[58] Field of Search ......................... 422/57; 424/36; 436/518, 527, 528, 531, 810, 823; 260/112 R

[56] References Cited

U.S. PATENT DOCUMENTS 4,234,563  11/1980  Rippe ..................................... 424/11
4,341,761   7/1982  Ganfield et al. ...................... 424/85
4,456,553   6/1984  Oshida et al. ........................ 424/88

OTHER PUBLICATIONS

American Hosp. Supply Corp., Chem. Abstracts, 92 (1980) #179002b.
Sato et al., Chem. Abstracts, 100 (1984) #154962k.
Asahi Chem. Ind. Co. Ltd., Chem. Abstracts, 94 (1981) #36396p.

Primary Examiner—Christine M. Nucker
Attorney, Agent, or Firm—Bertram I. Rowland

[57] ABSTRACT

Compositions, articles of manufacture, and methods are provided for enhanced binding of compounds to a surface. The compositions find particular use in coating wells, slides, other surfaces, where ligands or receptors are to be bound and detrimental non-specific binding may be encountered. Particularly, proteins are modified by alkylation to produce a product which strongly adheres to a surface, allows ligands and receptors to be firmly attached by means of the alkylated protein to a surface under mild non-denaturing conditions and permits procedures to minimize non-specific binding of proteins without significant loss of the materials of interest.

9 Claims, No Drawings

METHOD AND COMPOSITION FOR PROTEIN IMMOBILIZATION

BACKGROUND OF THE INVENTION

1. Field of the Invention

A large number of processes are involved where aqueous protein solutions are employed and it is necessary to provide specific binding of organic compounds, such as proteins, to a solid surface while substantially eliminating or reducing non-specific binding. In many assays, involving ligands, such as proteins, enzymes, and haptens, and/or receptors, one attempts to bind a compound to a surface firmly enough to maintain the compound at the surface while employing procedures for eliminating non-specific binding. Other considerations are the effect of conjugating of proteins to non-proteinaceous materials, where changes in the natural characteristics of the protein may result, as well as adsorption on a non-proteinaceous surface. There is, therefore, a need to provide means for controlled binding of ligands to a surface, where the ligand may be subsequently subjected to aqueous solutions of proteins followed by one or more washing steps to remove non-specifically bound protein.

2. Description of the Prior Art

Various methods of adhering proteinaceous compositions to solid surfaces may be found in the following U.S. Pat. Nos.: 1,873,691; 1,915,048; 3,556,945; 3,705,084; 3,983,000; 3,966,580; 4,124,700; 4,182,655; 4,210,722; and 4,054,646.

SUMMARY OF THE INVENTION

Proteinaceous compositions are employed for modifying the binding characteristics of articles of manufacture for use in combination with aqueous solutions of a compound, particularly where a ligand or receptor is bound to a surface. The proteinaceous compositions are lower alkylated proteins, primarily alkyl esters, which adhere strongly to a variety of solid surfaces and provide means for linking compounds to the surfaces. The articles-of-manufacture find particular use in various assays.

DESCRIPTION OF SPECIFIC EMBODIMENTS

Novel proteinaceous compositions are prepared for coating a wide variety of surfaces, where the proteinaceous coating adheres tenaciously to the surface and acts as an intermediate for the permanent binding of compounds to the surface, particularly during procedures for removing non-specifically bound materials. The proteinaceous compositions allow for easy removal of non-specifically bound proteins, so that background resulting from such non-specific binding is significantly minimized.

The proteinaceous compositions to be used as the linking intermediate layer on a solid surface are readily prepared by alkylation of an appropriate poly(amino acid) (includes polypeptides and proteins) of at least about 10,000 molecular weight, preferably at least about 30,000 molecular weight and conveniently from about 30,000 to 600,000 molecular weight. The alkylation is carried out in a polar solvent and, depending upon the method of alkylation, the polar solvent may also be the alkylating agent. The protein is dissolved in the solvent and alkylated under relatively mild conditions, generally at a temperature of from about 10–50° C., more usually at a temperature of from about 15–30° C. for a sufficient time to provide the desired degree of alkylation, primarily producing alkyl esters, although other reactions may occur to some extent, e.g., etherification, peptide formation, etc. Times for the reaction will generally be at least about six hours and not more than about six days. The resulting product should be insoluble in aqueous methanol and water, but soluble at least 0.01% in 0.3% Triton X100. Usually at least about 20%, more usually at least about 40% and less than about 90%, usually less than about 75% of the available carboxyl groups will be esterified.

Various alkylating agents may be employed, such as alkanols, alkyl esters of inorganic acids, alkyl halides, and the like. The alkyl group will generally be of from one to three carbon atoms, usually of from one to two carbon atoms, preferably one carbon atom, i.e. methyl.

The preferred method of alkylation is to use cold methanolic HCl at about 0.01 to 0.1N, usually of from about 0.03 to 0.08, preferably about 0.06N. After the reaction is sufficiently completed, upon addition of water, usually at least an equal volume to the methanol volume, more usually from about two to ten times, preferably about four times, the product precipitates out. Small molecular weight compounds may then be removed by dialysis with dilute HCl, generally less than about 0.005N and the retentate lyophilized and stored. For use, the lyophilized product is dissolved in an aqueous solvent containing a non-ionic detergent, e.g. polyethylene glycol, polypropylene glycol, combinations thereof, as well as esters and ethers thereof. The resulting solution will usually contain the protein at a concentration in the range from about 0.005 to 1 weight percent, more usually from about 0.005 to 0.1 weight percent, preferably about 0.01 to 0.05 weight percent.

A wide variety of materials may be coated. The materials may be glass, various plastics, such as polystyrene, polyacrylates, polyvinyl halides, e.g., polyvinyl chloride, silicones, various latexes, and the like. These materials may be surfaces of test tubes, slides, wells, cups, microtiter plates, plates, or the like. The solution may be applied to the well by any convenient means, such as dipping, spraying, coating, drying, or the like. The surface to be coated should be sufficiently wetted to ensure that a thin coating of the alkylated proteinaceous composition remains. The coating may be applied at ambient or slightly elevated temperatures, generally ranging from about 20° to 50° C., more usually from about 25° to 40° C., where the aqueous solution is allowed to evaporate to leave a uniform proteinaceous composition coat over the surface. Once the coat is dried it may be used directly in a variety of ways.

Compounds. e.g. ligands and labels, to be bound to the surface coated with the proteinaceous composition, may be small or large molecules, that is small organic molecules of about 125 to 2,000, more usually up to about 1,000 molecular weight, which may include drugs, dyes, fluorescers, hormones, lymphokines, lipids, or the like. More usually, the compound will be a poly(amino acid) which will include both ligands and receptors, generally ranging from about 2,000 to 1 million or more molecular weight, more usually from about 5,000 to 600,000 molecular weight. In addition, cells may be bound to the coated surface, which may include bacteria, fungi, protozoa, mammalian cells, or the like. In addition, viruses or other large assemblages may also be bound to the coated surface.

The lower molecular weight compounds, those below about 5,000 molecular weight will normally be bound covalently to the coated surface, while compounds of 5,000 or more molecular weight may be bound either non-covalently or covalently, preferably covalently.

Non-covalent binding can be achieved by drying the solution of a protein onto the surface of the alkylated proteinaceous composition coating of the subject invention. Alternatively, various covalent crosslinking agents may be employed to covalently bond compounds, e.g. proteins, to the alkylated proteinaceous composition, such as bifunctional reagents illustrated by glutaraldehyde, bis-didiazobiphenyl, the sulfite salt of diazobenzoic acid, etc. Alternatively, reagents can be used which provide for specific binding, such as activated olefins, such as maleimide, which can be linked to a protein employing p-maleimidobenzoic acid and the other protein to be linked modified, in the absence of available thiol groups, by employing Ellman's reagent, methyldithioacetic acid, etc., and reducing the disulfides with dithiothreitol. The resulting mercaptides may be bonded to the activated olefins in accordance with conventional ways.

The subject invention finds particular use in situations where one wishes to measure specific binding between a ligand and receptor on a solid surface, where the measurement results from a label bonded to one of the specific binding pair members present in solution. Where the labeled member may adhere strongly in a non-specific manner, to the surface to which one of the specific binding members is originally bound, a large background may interfere with detection of a positive result. While washing may diminish the background, the amount of washing is limited, since it also results in loss of specifically bound label. Thus, by employing the alkylated proteinaceous composition as an intermediate for binding a compound to a solid surface, extensive washing can be employed to substantially reduce the non-specific adherence of components of the assay medium, without loss of the specifically bound label. Therefore greatly enhanced sensitivity of assays and reduced probability of error are achieved.

One can have a ligand or receptor bound to the alkylated proteinaceous film. In one aspect, one carries out the assay where the specific binding pair member bound to the surface by means of the alkylated proteinaceous composition competes for its complementary member with the analyte in the medium. Alternatively where the analyte is a polyvalent analyte, such as an antigen or antibody, the analyte may act as a bridge to bind the labeled complementary member to a solid surface.

After carrying out the assay in accordance with the particular assay method, the surface may be washed from about one to ten or more times with a buffered solution, conveniently phosphate buffered saline, containing a small amount of protein, generally from about 0.5 to 2 weight percent of an albumin or globulin, particularly serum albumin, and a small amount of a detergent, generally from about 0.1 to 0.5 percent of a non-ionic detergent. These latter particular components are not critical, and the washing will vary depending upon the assay, the materials involved, the label, and the manner of detection. After washing the surface free of non-specifically bound materials, the label bound to the surface may then be detected in the absence of significant background. The particular manner of detection will depend upon the label, different techniques being used for radionuclides, fluorescers, enzymes, and the like.

The following examples are offered by way of illustration and not by way of limitation:

EXPERIMENTAL

Methylation of Bovine Serum Albumin (BSA)

Into 50 ml cold absolute methanol was added 0.5 g bovine serum albumin (BSA) and conc. HCl to 0.06N (0.25 ml) and the mixture allowed to stand at room temperature for 3 days. To the mixture was then added 200 ml cold water and the precipitate dialyzed against 0.001N HCl. The precipitate was lyophilized and stored.

To obtain 0.01% Met. BSA coating solution, sufficient of the lyophilized material is dissolved in 0.3% Triton X-100 in phosphate buffered saline plus 0.04% sodium azide and the insoluble material filtered and weighed. Sufficient additional lyophilized material is added until the final dissolved concentration is 0.01%.

Employing radioactive methanol, the added methyl groups were equal to about 60% of the available carboxyl groups. The average number of methyl groups attached to a BSA molecule by the method of the present invention was determined as follows. Methylation was performed as described above employing [$^{14}$C]-labeled methanol (1720$\mu$Ci/mg) diluted in methanol to a specific activity of $1.26 \times 10^{-3} \mu$Ci/mg ($2.36 \times 10^3$ cpm/mg). After methylation, the [$^{14}$C]-methylated BSA was dialyzed exhaustively to remove all methanol, then dried and counted. Five mg of the [$^{14}$C]-methylated BSA was found to have a net count of 370 cpm, corresponding to 0.157 mg (370 cpm/$2.36 \times 10^3$ cpm/mg) of methanol per 5 mg of methylated BSA. This is equivalent to about 65 molecules of methanol per molecule of BSA. There are 96 carboxyl groups in BSA.

Coating of Microtiter Plate Wells

The wells of microtiter plates (Dynatech Laboratories, Inc.) are first covered with 50 $\mu$l of 0.01% methylated bovine serum albumin (prepared as described above) in PBS containing 0.3% Triton X-100 and 0.5% sodium azide, dried overnight at 37° C., then rinsed twice with PBS and then treated with 0.25% glutaraldehyde for 1 hour at room temperature. After a rinse with PBS, the surface is now ready to be used for covalent linking with an amino-containing compound. After the specific protein or other compound is attached to the Met-BSA coated wells (as described below) the wells are incubated for 2 hours with 0.5% glycine in PBS to react with any unreacted aldehyde groups.

Employing the above surfaces, coated or uncoated with Met-BSA, either with or without the glutaraldehyde treatment, two different series of experiments were performed using two different protein analytes.

Experiment (a) in Table 1 demonstrates that coating the wells with Met-BSA greatly enhances binding of the highly water soluble protein, BSA, to the well surface. Even greater binding is obtained by covalently linking the $^{125}$I-BSA to the wells coated with methylated BSA by means of glutaraldehyde.

Experiment (b) in Table 1 demonstrates the enhanced binding of an insoluble protein mixture, represented by human milk fat globule membrane proteins (HMFG), with the Met-BSA coated surfaces. As was the case with $^{125}$I-BSA, a much higher binding of HMFG was obtained when precoating the wells with methylated BSA and even higher binding is obtained by covalently binding the HMFG to the methylated BSA coated plates with glutaraldehyde.

TABLE 1
Effect of precoating with Methylated bovine serum albumin (Met-BSA) on binding of proteins to a solid plastic surface.

| Protein bound | Treatment of Solid Surface | cpm bound | % cpm bound |
|---|---|---|---|
| Experiment a[1] | | | |
| $^{125}$I-BSA[1] (16 ng) | none | 19,400 ± 598 | 10% |
| $^{125}$I-BSA (16 ng) | Met-BSA[3] | 54,531 ± 2481 | 27% |
| $^{125}$I-BSA (16 ng) | Met-BSA + glutaraldehyde | 75,101 ± 1521 | 38% |
| Experiment b[2] | | | |
| HMFG (3 ng) | none | 2,471 ± 115 | — |
| HMFG (3 ng) | Met-BSA | 9,461 ± 316 | — |
| HMFG (3 ng) | Met-BSA + glutaraldehyde | 12,458 ± 169 | — |

[1] A solution of $^{125}$I-labeled bovine serum albumin ($^{125}$I-BSA) was dried onto a plastic surface of wells (16 ng/well) of microtiter plates (Dynatech, polyvinyl chloride) treated or untreated as indicated. The wells are washed 5× with RIA buffer (phosphate-buffered saline + 1% BSA + 0.3% Triton X-100 and then cut from the plate and counted for radioactivity.
[2] A solution containing delipidated human milk fat globule (HMFG) was dried on wells (3 ng/well) of Dynatech microtiter plates that were treated or untreated as indicated, then unreacted glutaraldehyde was reacted with 0.5% glycine solution. The HMFG on the solid phase was detected by incubating the wells first with a mouse monoclonal antibody (BLMRL-HMFG-Mc5) that detects a component of HMFG, then the relative amount of the mouse monoclonal antibody bound was determined with an $^{125}$I-labeled rabbit anti-mouse IgG.
[3] Methylated BSA prepared as described above.

In an experiment, the results of which are shown in Table 2, to demonstrate the tenacity of binding of Met-BSA to wells of microtiter plates, binding of $^{125}$I-Met-BSA to that of $^{125}$I-BSA was compared. Only 10% of the $^{125}$I-BSA remained bound to the plastic surface after 5 washes with RIA buffer, while at least 90% of the $^{125}$I-Met-BSA remained attached after 9 washes. The fact that all of the loss in the $^{125}$I-Met-BSA experiment occurred during the first 2 washes with PBS suggests that the counts washed away are non-covalently attached $^{125}$I and that even less of the Met-BSA is removed by the washing. See Table 2.

TABLE 2
Comparison of Binding of $^{125}$I-labeled Met-BSA and $^{125}$I-BSA to Plastic Wells[1]

| Treatment of Well | cpm ± S.D./Well | Percentage of cpm remaining |
|---|---|---|
| $^{125}$I-BSA: | | |
| 5 × RIA | 19,400 ± 598 | 10%[2] |
| $^{125}$I-Met-BSA: | | |
| None | 215,980 ± 5,000 | 100% |
| 2 × PBS | 195,800 ± 870 | 91% |
| 2 × PBS + Glutar + Gly | 189,630 ± 7,390 | 88% |
| 2 × PBS + Glutar + Gly + 5 × RIA | 195,700 ± 9,770 | 91% |

[1] Equal amounts of $^{125}$I-labeled Met-BSA or $^{125}$I-BSA in 50 μl aliquots were applied to wells of microtiter plates (Dynatech, polyvinyl chloride) and allowed to dry overnight. Quadruplicates were treated as indicated and then the bottoms of the wells were cut off and counted. (2 × PBS) = washed 2 times with phosphate buffered saline. (Glutar.) = incubated with 0.25% glutaraldehyde in PBS for 1 hour. (Gly.) = rinsed 1 time with 0.5% glycine in PBS. (5 × RIA) = washed 5 times with RIA buffer (see above).
[2] $^{125}$I-BSA added to each well had an average of 194,000 cpm.

The next study demonstrates the use of the subject invention for screening monoclonal antibodies. Into each well was added 10 μl containing 6 ng of delipidated HMFG dissolved by sonication in PBS plus 0.3% Triton X-100 and allowed to dry overnight. The plates were then washed with PBS, treated for 2 hours with 0.5% glycine in PBS, washed twice more with PBS and let dry and stored at room temperature until use.

A solid phase binding test was performed by adding an appropriate dilution of hybridoma culture supernatant containing antibody or control culture media to the wells with bound antigens. Antibody dilution was done in RIA buffer, containing 0.3% Triton X-100, 1% BSA and 0.05% sodium azide in PBS. The wells were then covered with transparent adhesive tape to prevent evaporation and agitated overnight on a rotary agitator. The wells were then washed 5 times with RIA buffer, and $10^5$ cpm $^{125}$I-labeled, affinity purified, rabbit anti-mouse immunoglobulin dissolved in RIA buffer were added. The plates were then incubated with agitation as before for 3 hours at room temperature, washed 5 times with RIA buffer, the bottom of wells cut from the plate and counted for radioactivity. Positive and negative controls were included in each assay. The assays were highly reproducible with very low standard errors of mean. The results are reported in Table 3.

TABLE 3
Radioimmunobinding assay of monoclonal antibody BLMRL-HMFG-Mc5 to 6 ng of delipidated HMFG attached to the solid phase.*

| Culture medium | cpm bound/well |
|---|---|
| BLMRL-HMFG-Mc5 | 18,846 ± 535** |
| Controls | |
| P3/NS1/1Ag4-1 (myeloma medium) | 679 ± 48 |
| Fresh medium | 731 ± 102 |

*Culture medium from hybridoma culture or control medium were used undiluted.
**Standard error of mean.

In another experiment cell membranes were attached to microtiter plate wells by procedures similar to those described above in order to detect surface membrane antigens by monoclonal antibodies. In order to obtain cell membranes from the different cell lines to be bound to the microtiter plates, the separation was started with 2 ml of packed cells that were scraped from their substrates with a rubber policeman. The cells were then washed 3 times with PBS and once with buffer A (0.25 M sucrose, 14 mM Tris buffer, pH 7.5). The cell pellets were resuspended in 30 ml of 3M glycerol in 15 mM Tris buffer, pH 7.5, at 4° C. and left at this temperature for 30 min. The cells are then spun at 1500 xg at 4° C. and the resulting cell pellet resuspended in 30 ml of 1 mM MgCl$_2$ in 15 mM Tris buffer pH 7.5, and then homogenized with a tight fitting Teflon-pestle homogenizer, while kept in an ice bath. The homogenates are then spun at 165 xg at 4° C. for 45 sec and the pellet discarded. The supernatant is spun at 700 xg for 20 min at 4° C. The resulting pellet is resuspended in buffer A up to a final volume of 4 ml. The resulting suspension is layered on a sucrose gradient prepared in a tube to fit a SS-90 vertical rotor (Sorvall). The sucrose gradient consisted of a 6 ml cushion of 75% sucrose solution (w/w) in buffer A, 16 ml of a 20 to 50% sucrose gradient in 15 mM Tris buffer, pH 7.5, and 9 ml of 20% sucrose in 10 mM Tris buffer, pH 7.5. The layers of the tube were introduced in the order given. The gradient is then spun at 15,000 rpm for 30 min at 4° C. in a SS-90 Sorvall vertical rotor. After the spin, the visible band is harvested from the 20 to 50% gradient. The resulting membranes are then bound to the surface by the glutaraldehyde procedure described above.

Three monoclonal antibody compositions against normal breast epithelial cell membranes were prepared and various cell membranes tested to determine breast specificity of these monoclonal antibodies. The specificity was determined with the cell membranes of breast and non-breast cell lines on the solid phase with radioimmunobinding assay. It was shown that the three antibodies, BLMRL-HFMG-Mc3, -Mc5, and -McR2 all bound to membranes of breast epithelial cell lines but not to those of non-breast lines. Because of the greater sensitivity of this test, low concentrations of these antigens could be detected. See Table 4.

TABLE 4

Specificity of monoclonal antibodies against breast epithelial cell surface components determined by solid phase radioimmunobinding assay.

| Cells | Condition | Mc3 | Mc5 | Mc7 |
|---|---|---|---|---|
| HMFG | Suspension | +* | + | + |
| MCF-7 | Monolayer | + | + | + |
| SKBR-3 | Monolayer | + | + | + |
| BT-20 | Monolayer | + | + | + |
| HeLa | Monolayer | − | − | − |
| HT-29 | Monolayer | − | − | − |
| Breast Fibroblasts | Monolayer | − | − | − |

*Indicates that value for sample was at least 2 × the value obtained for non-specific control.

The subject invention provides for a simple way to stably bind compounds to a surface and to greatly improve specific binding, reproducibility and the sensitivity of solid phase determinations employing labeled entities; the invention allows for extensive washings to remove non-specifically bound entities to container or support surfaces. Furthermore, the subject compositions provide for a strongly adhering layer which is highly functionalized to allow for covalently linking of a wide variety of materials, both ligands and receptors, to the surface, which are then permanently bound to the surface. The compositions can be easily prepared and can be used with simple methods for coating a wide variety of surfaces. The coatings provide for binding easily inactivated or denatured substances under mild conditions to the surface. The binding is sufficiently stable, so that the specifically bound compounds can be retained during procedures for removal of non-specifically bound materials. The subject method finds particular application where labeled antigens and antibodies are involved, where serum or other protein-containing sample is employed, or other situations where there may be large amounts of protein in the medium as compared to the material of interest or the reagent.

Although the foregoing invention has been described in some detail by way of illustration and example for purposes of clarity of understanding, it will be obvious that certain changes and modifications may be practiced within the scope of the appended claims.

What is claimed is:

1. In a method for carrying out a diagnostic assay, wherein at least one of the analyte and reagent are a poly(amino acid), and the analyte is a member of a specific binding pair consisting of ligand and receptor, wherein one of said specific pair is bound to a solid surface, and the analyte is determined by the binding of analyte to its complementary member bound to the solid support, the improvement which comprises employing as a support a solid support coated with an alkylated poly(amino acid) of at least about 30,000 molecular weight, wherein said alkyl groups are from one to three carbon atoms, said alkylated poly(amino acid) being insoluble in water at 25° C. and soluble to at least 0.01 weight percent in an aqueous solution of a non-ionic detergent present in at least about 0.005 weight percent.

2. A method according to claim 1, wherein a ligand or receptor is bound to said alkylated poly(amino acid).

3. A method according to claim 2, wherein said alkyl is methyl.

4. A method according to claim 3, wherein said alkylated poly(amino acid) is methylated bovine serum albumin, which is methylated employing absolute methanol and HCl.

5. An article of manufacture comprising a solid support coated with an alkylated poly(amino acid) of at least about 30,000 molecular weight, wherein said alkyl groups are from one to three carbon atoms, said alkylated poly(amino acid) being insoluble in water at 25° C. and soluble to at least 0.01 weight percent in an aqueous solution of a non-ionic detergent present in at least about 0.005 weight percent.

6. An article of manufacture according to claim 5, wherein said alkyl is methyl and said non-ionic detergent is present in about 0.01% and is Triton X-100.

7. An article of manufacture according to claim 5, wherein said alkyl is methyl and methylation is performed with absolute methanol and HCl at moderate temperatures to alkylate at least about 40% of the available carbonyl groups.

8. An article of manufacture according to claim 5, wherein a ligand or a receptor is bound to said poly(amino acid).

9. An article of manufacture according to claim 5, wherein said poly(amino acid) is bovine serum albumin.

* * * * *